(12) United States Patent  
Boucher et al.

(10) Patent No.: US 6,514,274 B1
(45) Date of Patent: Feb. 4, 2003

(54) METHOD AND APPARATUS FOR ROTATOR CUFF REPAIR

(75) Inventors: James Boucher, Warsaw, IN (US); Kevin J. Kessler, Boca Raton, FL (US)

(73) Assignee: Arthrotek, Inc., Warsaw, IN (US)

( * ) Notice: Subject to any disclaimer, the term of this patent is extended or adjusted under 35 U.S.C. 154(b) by 0 days.

(21) Appl. No.: 09/512,961

(22) Filed: Feb. 25, 2000

(51) Int. Cl.[7] ............................................. A61B 17/04
(52) U.S. Cl. ...................................... 606/232; 606/69
(58) Field of Search ................................ 606/232, 233, 606/69; 623/13.11, 13.12, 13.13, 13.14, 19.11, 23.11, 23.12, 23.13, 23.14

(56) References Cited

U.S. PATENT DOCUMENTS

| | | | |
|---|---|---|---|
| 2,765,787 A | | 10/1956 | Pellet |
| 3,896,500 A | * | 7/1975 | Rambert et al. ............... 128/92 |
| 5,195,542 A | * | 3/1993 | Gazielly et al. ............ 128/898 |
| 5,306,301 A | | 4/1994 | Graf et al. |
| 5,527,341 A | * | 6/1996 | Gogolewski et al. ........ 606/232 |
| 5,593,425 A | * | 1/1997 | Bonutti et al. ............... 606/220 |
| 5,634,926 A | * | 6/1997 | Jobe ........................... 606/101 |
| 5,735,875 A | * | 4/1998 | Bonutti et al. ............... 606/220 |
| 5,904,683 A | * | 5/1999 | Pohndorf et al. .............. 606/61 |
| 6,013,083 A | * | 1/2000 | Bennett ....................... 606/104 |
| 6,041,485 A | * | 3/2000 | Pedlick et al. ................. 29/450 |
| 6,063,106 A | * | 5/2000 | Gibson ........................ 606/232 |
| 6,093,201 A | * | 7/2000 | Cooper et al. ............... 606/232 |
| 6,146,408 A | * | 11/2000 | Bartlett ........................ 606/232 |
| 2001/0041938 A1 | * | 11/2001 | Hein ........................ 623/13.13 |
| 2001/0051815 A1 | * | 12/2001 | Esplin ........................ 606/232 |

OTHER PUBLICATIONS

"Single Incision Fixation . . . EndoButton. As Easy as Passing the Graft", by Acufex Microsurgical, Inc. from The Journal of Arthroscopic & Related Surgery, vol. 11, No. 5; Oct. 1995 (2 sheets).

Cuff Link, Bone Tunnel Augmentation Device by Innovasive Devices, Inc.; copyright 1997. (2 sheets).

Innovasive Devices, Inc. "Cuff Link—Bone Tunnel Augmentation Device," Copyright 1997 (2 sheets).

* cited by examiner

*Primary Examiner*—David O. Reip
*Assistant Examiner*—D. Jacob Davis
(74) *Attorney, Agent, or Firm*—Harness, Dickey & Pierce, P.L.C.

(57) ABSTRACT

A rotator cuff buttress plate adapted to support a load from at least one suture used in securing a rotator cuff relative to a humerus. The rotator cuff buttress plate includes an inner surface, an outer surface, a sidewall and a plurality of apertures. The inner surface is adapted to engage an outer portion of a humerus. The outer surface is opposite the inner surface and is adapted to support the load from at least one suture. The sidewall is positioned between the inner surface and the outer surface. The suture is passed through the at least one aperture to distribute the suture load over the buttress plate.

14 Claims, 4 Drawing Sheets

METHOD AND APPARATUS FOR ROTATOR CUFF REPAIR

BACKGROUND OF THE INVENTION

1. Field of the Invention

This invention relates generally to a method and apparatus for use in an orthopedic surgical procedure and, more particularly, to a method and apparatus for rotator cuff repair.

2. Discussion of the Related Art

A natural shoulder may undergo degenerative changes due to a variety of etiologies. For example, patients that perform various repetitive shoulder movements in which the humerus is raised upward in a repetitive manner may cause impingement of the rotator cuff between the humerus and the clavicle of the patient. Overtime, this may cause a bone spur to be formed in this area. The resulting bone spur may abrade the rotator cuff during further shoulder movement, particularly upon raising the humerus. This abrasion may cause the rotator cuff to tear or become detached along the greater tuberosity of the humerus.

In order to reattach and secure the rotator cuff relative to the greater tuberosity of the humerus or repair the tear, several techniques have been employed. In one technique, a bone trough or groove is formed laterally across the greater tuberosity for placement of the rotator cuff. The rotator cuff is positioned within this bone trough and sutured in place by way of passing sutures through the rotator cuff and within bores drilled through the greater tuberosity. The sutures are weaved or stitched through the rotator cuff and passed through the multiple bores to retain the rotator cuff relative to the humerus. However, since the suture is passed directly through the bone from one bore into another, this may result in cutting of the bone along the bore and in worst case conditions, cutting right through the bone, thereby potentially causing the rotator cuff to again separate from the humerus. This condition may be further aggravated by braided sutures which may cause further abrasion to the bone.

Another technique utilizes suture anchors that are secured within the trough with the sutures passing out through the trough and into the rotator cuff. The sutures are then secured or tied relative to the rotator cuff to retain the rotator cuff relative to the humerus. However, in some patients, bone deterioration may exist in this area of the humerus, thereby inhibiting or providing less than optimal securement of the suture anchors within the trough. The sutures are also simply passed through the rotator cuff which may cause additional abrading or tearing of the rotator cuff since there is a point contact of the suture relative to the rotator cuff itself.

In yet another technique, cylindrical grommet shaped devices are inserted into enlarged bores passing through the humerus. As the suture is secured to the rotator cuff and passed through these enlarged bores, the suture is guided through the grommets. The grommets thus act to inhibit the suture from engaging the internal edges of the bores to reduce the cutting action of the suture relative to the bone. However, this technique also presents several disadvantages. For example, several individual grommet shaped devices are required for insertion into each bore formed into the humerus which may increase surgical time, cost and complexity. Additionally, since the grommets are inserted into enlarged bores and include only a slight lip adjacent the edge of the bores, the grommets may, in fact, be pulled within the bores, thereby reducing or eliminating the effect of the grommets from preventing cutting of the bone tissue. Likewise, a relative point contact is maintained between the suture and the grommet so that the suture force is not dispersed over a relatively large area, thereby potentially causing migration of the grommets in these areas. Finally, larger bores must be made to receive the grommets, thereby requiring additional bone to be removed which is generally not desired.

What is needed then is a method and apparatus for rotator cuff repair which does not suffer from the above mentioned disadvantages. This, in turn, will reduce or eliminate pull-out of sutures relative to the humerus, reduce or eliminate cutting of bone tissue by the sutures, distribute suture force or load over a large area both at the bone surface and at the rotator cuff surface, reduce or eliminate rotator cuff tearing from suture penetration and provide a cost effective and less complex surgical technique to repair rotator cuff tears. It is, therefore, an object of the present invention to provide such a method and apparatus for rotator cuff repair having the above benefits.

SUMMARY OF THE INVENTION

In accordance with the teachings of the present invention, a method and apparatus for rotator cuff repair is disclosed. The method and apparatus employs a rotator cuff buttress plate that supports and disperses a load from sutures employed to secure a rotator cuff relative to a humerus.

In one preferred embodiment, a rotator cuff buttress plate adapted to support a load from at least one suture used in securing a rotator cuff relative to a humerus includes an inner surface, an outer surface, a sidewall and a plurality of apertures. The inner surface is adapted to engage an outer portion of the humerus. The outer surface is opposite the inner surface and is adapted to support the load from the at least one suture. The sidewall is positioned between the inner surface and the outer surface. The at least one suture is passed through at least one aperture to distribute the suture load over the buttress plate.

In another preferred embodiment, a rotator cuff buttress plate system adapted to support a load from at least one suture used in securing a rotator cuff relative to a humerus includes a first buttress plate and a second buttress plate. The first buttress plate defines a plurality of apertures and is adapted to engage an outer portion of the humerus. The second buttress plate defines a second plurality of apertures and is adapted to engage an outer portion of the rotator cuff. The suture is passed through at least a first aperture from the first plurality of apertures and a second aperture from the second plurality of apertures to distribute the load from the suture over the first and second buttress plates.

In yet another preferred embodiment, a method for attaching a rotator cuff to a humerus includes forming a plurality of bone tunnels through the humerus, each having an entrance opening and an exit opening. The rotator cuff is then positioned atop the humerus adjacent to the entrance opening of the bone tunnels. A rotator cuff buttress plate is provided that defines a plurality of apertures that pass therethrough. The rotator cuff buttress plate is positioned adjacent the exit openings of the bone tunnels and a suture is passed through the rotator cuff, a first bone tunnel and a first aperture in the buttress plate. The suture is then secured relative to the rotator cuff and the buttress plate.

Use of the present invention provides a method and apparatus for rotator cuff repair. As a result, the aforementioned disadvantages associated with the currently available rotator cuff procedures and techniques have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning a method and apparatus for rotator cuff repair are merely exemplary in nature and are not intended to limit the invention or its application or uses. Moreover, while the present invention is discussed in detail below with respect to rotator cuff repair, the present invention may be employed with various other orthopedic procedures that require supporting a suture load over a bone.

Figure 1:
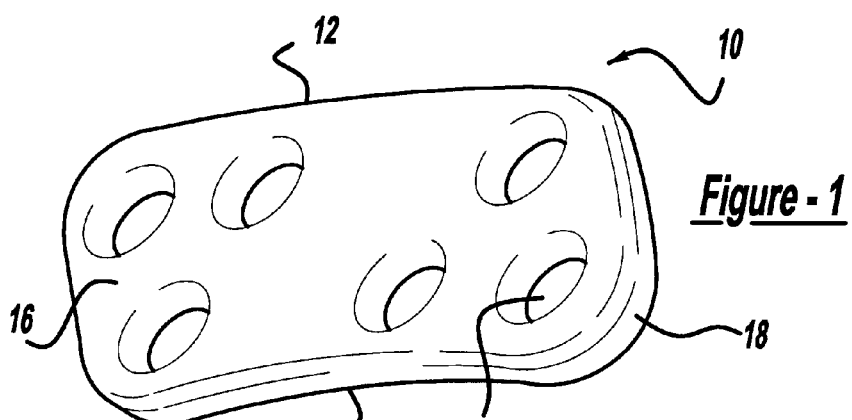
FIG. 1 is a perspective view of an apparatus for rotator cuff repair according to the teachings of the preferred embodiment of the present invention.

Referring to FIG. 1, a perspective view of an apparatus or a rotator cuff buttress plate 10 according to the teachings of the preferred embodiment of the present invention is shown. The buttress plate 10 includes an arcuate body 12 that includes an inner concave surface 14 and an outer convex surface 16. The inner concave surface 14 is shaped to nest with the greater tuberosity of a humerus and the outer convex surface 16 is adapted to retain and disperse the forces of a suture load, further discussed herein. Positioned between the inner concave surface 14 and the outer convex surface 16 is a trapezoidal shaped sidewall 18. While the body 12 of the rotator cuff 10 is shown having the particular configuration or shape set forth herein, it will understood that various other shapes may also be utilized depending upon where the plate 10 is employed and the relative shape and size of the particular patient.

The body 12 of the rotator cuff buttress plate 10 further defines a plurality of bores 20 passing through the body 12 from the outer convex surface 16 to the inner concave surface 14. Each bore 20 is defined by a substantially cylindrical sidewall portion 22 located adjacent the inner concave surface 14 and a substantially beveled or rounded sidewall 24 positioned adjacent the outer convex surface 16. The rounded sidewall 24 eliminates any sharp corners which may fray or cut a suture passing through the bore 20, further discussed herein.

Figure 2:
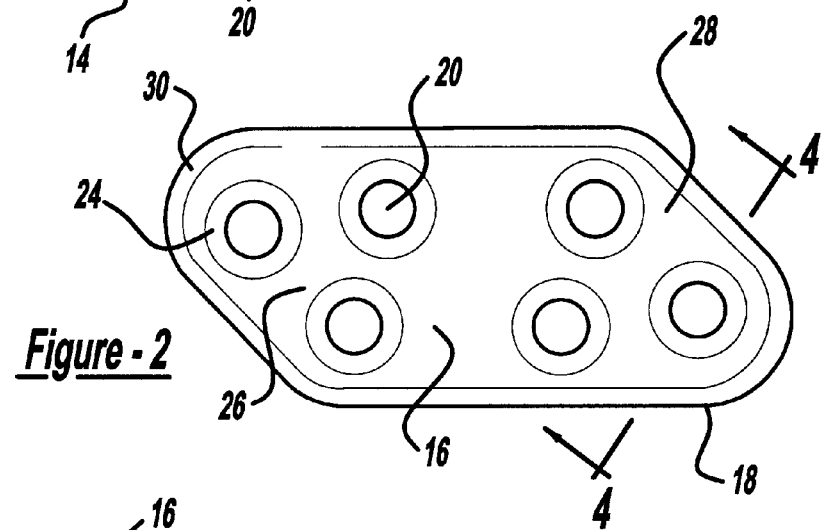
FIG. 2 is a top planar view of the apparatus of FIG. 1.
Figure 3:
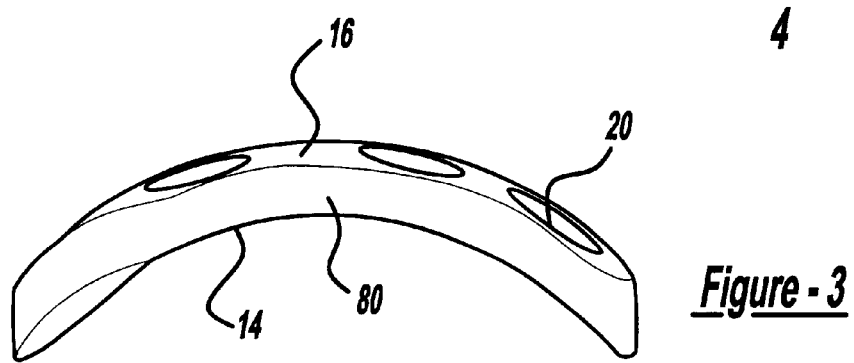
FIG. 3 is a side view of the apparatus of FIG. 1.
Figure 4:
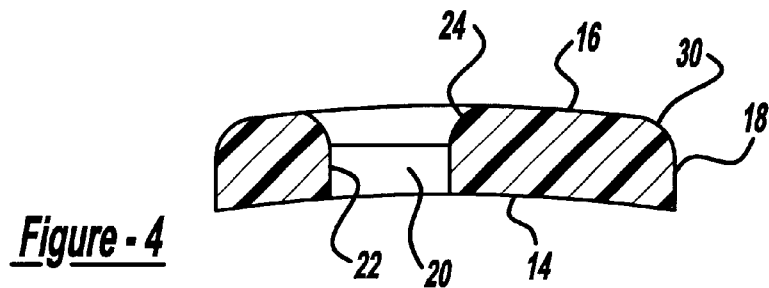
FIG. 4 is a cross sectional view of the apparatus of FIG. 1 taken along line 4—4 in FIG. 2.

The bores 20 are arranged in the body 12 to form corners of a pair of triangles, as shown clearly in FIG. 2. In this regard, a first triangular region 26 defined by a first set of bores and a second triangular region 28 formed from a second set of bores 20 are shown positioned relative to one another. Preferably, a suture will be grouped with either the first set of bores 20 associated with the first triangular region 26 or the second set of bores 20 associated with the second triangular region 28. In this way, substantially even distribution of the force or load exerted by the suture is dispersed or displaced in these triangular regions 26 and 28. However, the sutures may also cross between the first triangular region 26 and the second triangular region 28 in the associated bores 20 should this be desired to provide further distribution of the force exerted by the sutures over the bone. It should further be noted that the sidewall 18 also includes a rounded portion 30 located adjacent the outer convex surface 16 to also eliminate any sharp edges where a suture may be routed. In this regard, should a suture pass from outside the buttress plate 10 into one of the bores 20, the suture will engage the rounded sidewall portion 30 as opposed to a sharp corner.

The body 12 is preferably formed from a resorbable type material, such as LactoSorb® which is available from Biomet, Inc. of Warsaw, Indiana or any other type of resorbable material. In this regard, it should be noted that this type of resorbable material is translucent, thereby enabling visual alignment with bone holes found in a humerus, further discussed herein. The body 12 may also be formed from any other non-resorbable biocompatible material also, such as stainless steel, titanium, molybdenum, etc. Should LactoSorb® be utilized, the rotator cuff buttress plate 10 will generally be resorbed within about nine (9) to fifteen (15) months of implanting. In this regard, the structural integrity of the resorbable body 12 is maintained substantially throughout the healing time which is about six (6) to eight (8) weeks. Should a non-resorbable biocompatible material be utilized, the rotator cuff buttress plate 10 will simply remain in place.

Figure 5A:
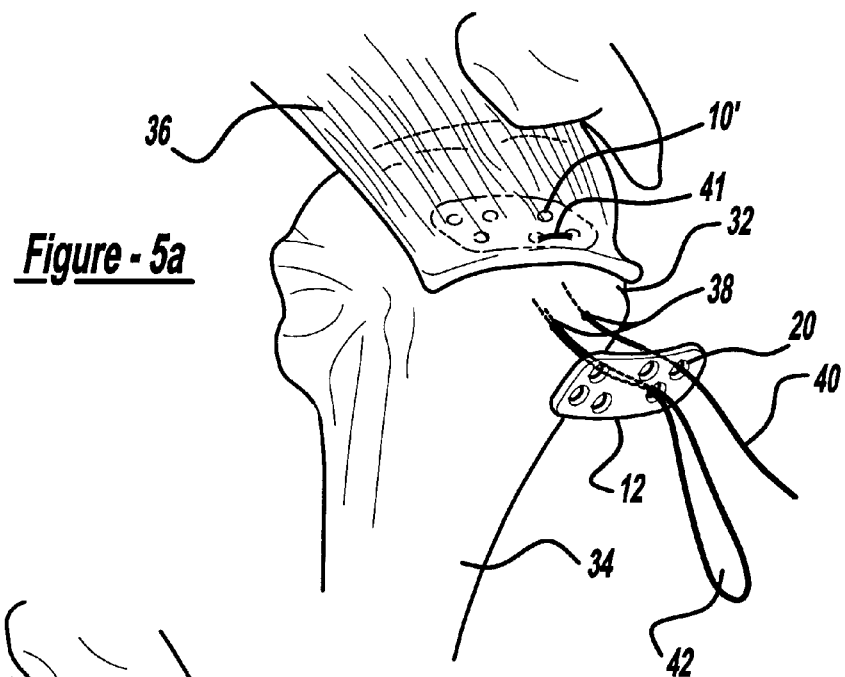
FIGS. 5A–5D illustrate a method for rotator cuff repair using the apparatus of FIG. 1 according to the teachings of the preferred embodiment of the present invention.
Figure 5B:
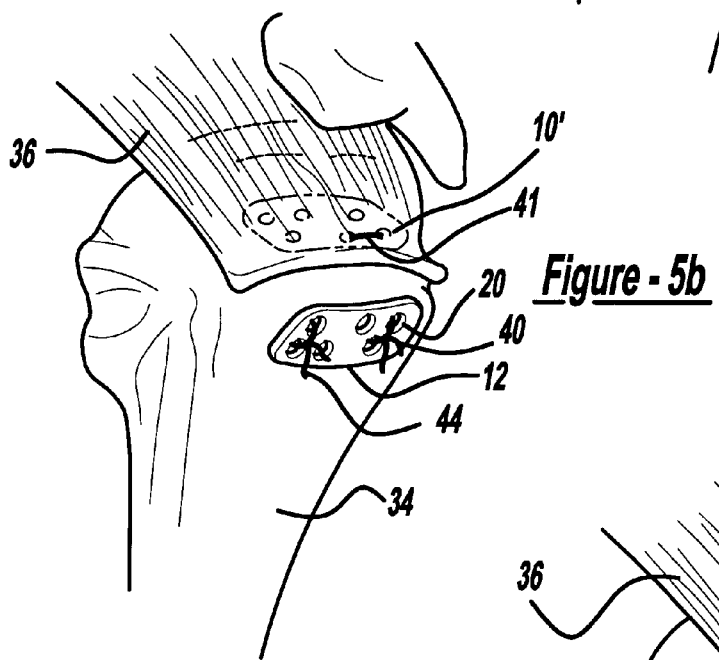
Figure 5C:
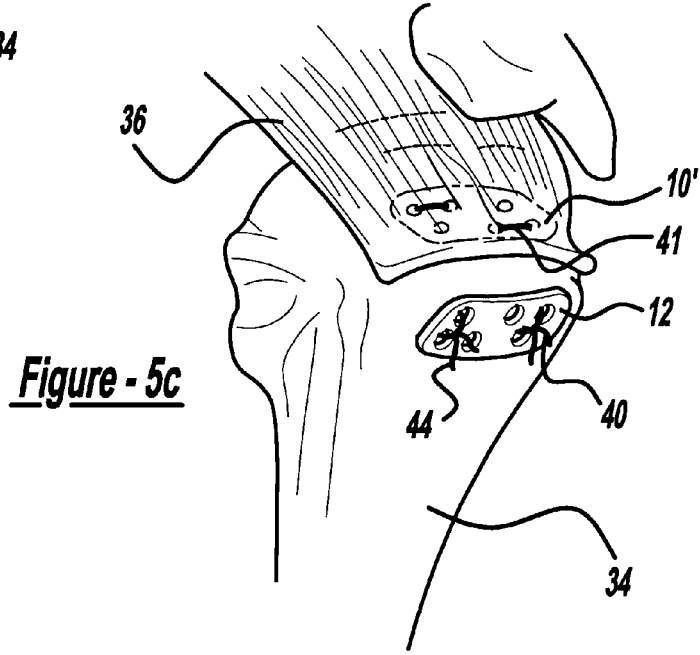
Figure 5D:
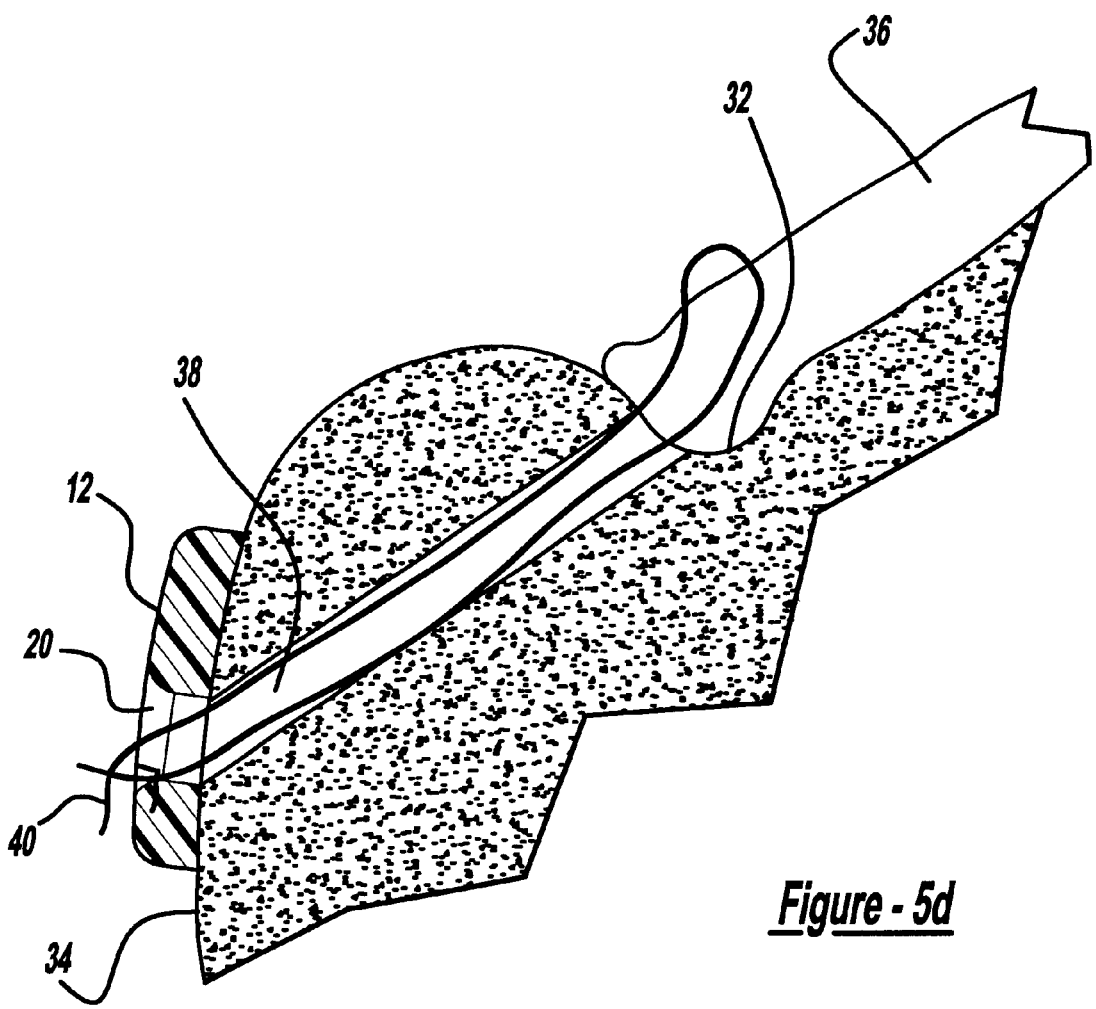

The method for implanting the rotator cuff buttress plate 10 according to the teachings of the preferred embodiment of the present invention will now be described with reference to FIGS. 5A–5D. Initially, a bone trough or groove 32, as shown clearly in FIG. 5D, is formed in the superior portion of the greater tuberosity of the humerus 34. Once the bone trough 32 is formed in the humerus 34, by way of any appropriate instrument, multiple bone holes or tunnels 38 having entrance and exit openings are drilled through the greater tuberosity of the humerus 34 from the bone trough 32 to the inferior region of the greater tuberosity. Once the bone trough 32 and the bone holes 38 are formed in the humerus 34, the rotator cuff 36 is positioned along the bone trough 32 for subsequent securement, via a suture 40 or any other appropriate material such as a flexible wire, etc.

In this regard, the rotator cuff buttress plate 10 is positioned adjacent to the superior portion of the greater tuberosity of the humerus 34 with the bores 20 aligned substantially with the bone holes 38 formed in the humerus 34. Since the buttress plate 10 is translucent, alignment of the bores 20 relative to the holes 38 is easily achieved. The suture 40 is then passed through one of the bores 20 in the buttress plate 10, threaded through a bone hole 38 and out through the bone trough 32. The suture 40 is then threaded out through the rotator cuff 36. The suture 40 is again passed down through the rotator cuff 36 to form a loop 41 of suture 40 over the rotator cuff 36, into the bone trough 32, through an additional bone hole 38 and out an additional bore 20 in the buttress plate 10. The suture 40 may then be returned through the same path forming a loop 42 with the suture 40. The end of the suture 40 extending at the rotator cuff 36 may be knotted or tied relative to the rotator cuff 36 with the other end of the suture 40 extending out from the buttress plate 10 passing through the loop 42 and knotted to retain the buttress plate 10 relative to the humerus, as shown in FIG. 5B.

With the suture 40 secured in the first triangular region 26, a subsequent suture 44 may be passed through additional bone holes 38 in the humerus 34 and secured to the second triangular region 28 in the same manner to firmly retain the rotator cuff 36 within the bone trough 32 formed in the humerus 34. The step of passing additional sutures through the humerus 34 and into the bores 20 in the buttress plate 10 may be repeated multiple times to assure that the rotator cuff 36 is firmly pulled and secured into the bone trough 32. Of course, the sutures 40 and 44 may be secured and routed in any manner the surgeon desires and the routing shown herein is merely exemplary.

One can observe that use of the buttress plate 10 inhibits the various sutures 40 and 44 from cutting the bone or humerus 34 adjacent the bone holes 38 by eliminating a point loading in these regions to a distributed load which is distributed substantially evenly over the buttress plate 10. In this regard, by providing a sufficiently large surface area for the buttress plate 10 relative to the bone 34, the force vectors (i.e., suture load) created by the tightened sutures 40 and 44 are dispersed through the plate 10. By distributing this suture load over a larger planar area which cover each of the bone holes 38 in the humerus 34, a more balanced and even distribution of the force exerted by the sutures 40 and 44 is achieved to thereby reduce or inhibit any cutting of the bone or humerus 34 by way of the sutures 40 and 44.

Finally, should the rotator cuff 36 itself be somewhat weakened or degraded in the attachment area or the superior region of the greater tuberosity of the humerus 34 be degraded, an additional buttress plate 10', as shown in phantom may be secured over the rotator cuff 36 itself. In this regard, the rotator cuff 36 is essentially sandwiched between two (2) buttress plates 10 and 10' with the sutures 40 and 44 passing through each buttress plate 10 and 10' to provide for additional fixation and securement of the rotator cuff 36 relative to the humerus 34. Such a configuration also evenly distributes the suture force or load from the sutures 40 and 44 evenly over the rotator cuff 36, via the buttress plate 10' versus simply passing the sutures 40 and 44 over the rotator cuff 36 itself which may cut or abrade the rotator cuff 36.

The rotator cuff buttress plate 10 therefore prevents cutting of the humerus 34 by way of the sutures 40 and 44 which pass through the bone holes 38. The rotator cuff buttress plate 10 achieves this by eliminating point loading of the sutures 40 and 44 relative to the holes 38 to a load distributed over the substantially planar rotator cuff buttress plate 10. Additionally, by use of a rotator cuff buttress plate 10' atop the rotator cuff 36 itself, a distributed load may also be achieved over the rotator cuff. 36 to eliminate or reduce any cutting of the rotator cuff 36, via the sutures 40 and 44. Finally, the rotator cuff buttress plate 10 may also be formed from a resorbable material such that it will resorb over time after the patient has fully healed.

Figure 6:
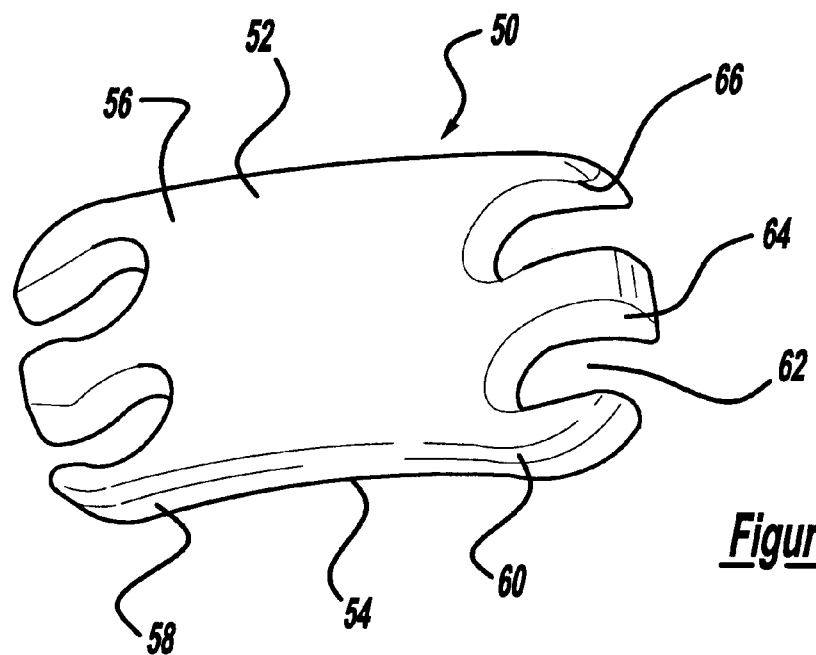
FIG. 6 is a perspective view of an apparatus for rotator cuff repair according to the teachings of another preferred embodiment of the present invention.
Figure 7:
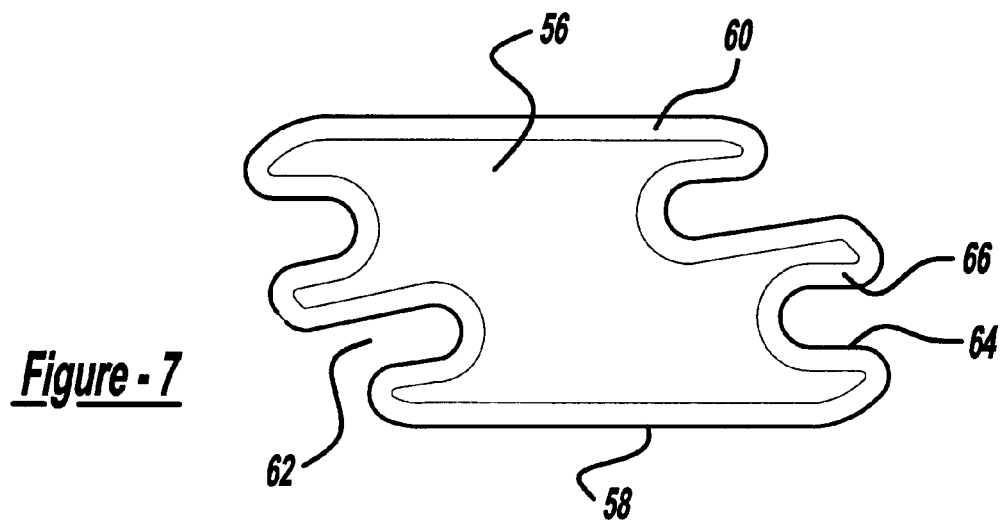
FIG. 7 is a top plainer view of the apparatus of FIG. 6.

Turning now to FIGS. 6 and 7, a rotator cuff buttress plate 50 according to the teachings of another preferred embodiment of the present invention is shown. The rotator cuff buttress plate 50 is substantially similar to the rotator cuff buttress plate 10 and includes an arcuate body 52 having an inner concave surface 54 in an outer convex surface 56. Here again, the inner concave surface 54 is shaped to nest with the greater tuberosity of a humerus and the outer convex surface 56 is adapted to retain and disburse the forces of a suture load. The rotator cuff buttress plate 50 also includes the trapezoidal shaped sidewall 58 having a rounded sidewall portion 60.

The rotator cuff buttress plate 50 defines a plurality of slots 62 which include a cylindrical sidewall 64 and a rounded sidewall 66. The slots 62 are adapted to be engaged by sutures 40 substantially similar to the rotator cuff buttress plate 10. In this regard, the sutures 40 are guided or passed through the slots 62 and are supported by the buttress plate 50 while the sutures also pass through the bone holes 38 in the humerus 34. Likewise, it is also contemplated that other shaped grooves, holes or bores may also be used with either rotator cuff buttress plate 10 or 50 to retain the sutures 40. The rotator cuff buttress plate 50 is also preferably formed from LactoSorb® or any other type of biocompatible material.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A method for attaching a rotator cuff to a humerus, said method comprising:
    forming a plurality of bone tunnels through the humerus, each having an entrance opening and an exit opening;
    positioning the rotator cuff atop the humerus adjacent to the entrance openings of the bone tunnels;
    providing a first rotator cuff buttress plate defining a plurality of apertures passing therethrough;
    positioning the first rotator cuff buttress plate adjacent to the exit openings of the bone tunnels;
    passing a suture through the rotator cuff, a first bone tunnel and a first aperture in the first buttress plate;
    providing a second buttress plate positioned atop the rotator cuff and passing the suture through the second buttress plate; and
    securing the suture relative to the rotator cuff and the first and second buttress plates.

2. The method as defined in claim 1 further comprising passing the suture through a second aperture in the first buttress plate, a second bone tunnel, and through the rotator cuff.

3. The method as defined in claim 2 wherein securing the suture relative to the buttress plate further includes tying the suture atop the buttress plate.

4. The method as defined in claim 1 further comprising forming a bone trough adjacent the entrance openings of the bone tunnels and positioning the rotator cuff within the bone trough.

5. The method as defined in claim 1 wherein providing the first buttress plate further includes providing a first buttress plate having an inner concave surface and an outer convex surface with the inner concave surface mating with an outer portion of the humerus.

6. The method as defined in claim 1 wherein passing the suture through the first and second buttress plates includes passing the suture through slots in the first and second buttress plates.

7. The method as defined in claim 1 wherein passing the suture through the first and second buttress plates includes passing the suture through holes in the first and second buttress plates.

8. A method for attaching a rotator cuff to a humerus, said method comprising:
    forming a plurality of bone tunnels through the humerus, each having an entrance opening and an exit opening;
    positioning the rotator cuff atop the humerus adjacent to the entrance openings of the bone tunnels;

providing a rotator cuff buttress plate defining a plurality of apertures passing therethrough;

positioning the rotator cuff buttress plate atop the rotator puff and adjacent to the entrance openings of the bone tunnels;

passing a suture through a first aperture in the buttress plate, the rotator cuff, and a first bone tunnel; and securing the suture relative to the rotator cuff and the buttress plate.

9. The method as defined in claim 8 wherein passing the suture through the buttress plate includes passing the suture through slots in the buttress plate.

10. The method as defined in claim 8 wherein passing the suture through the buttress plate includes passing the suture through holes in the buttress plate.

11. The method as defined in claim 8 further comprises passing the suture through a second aperture in the buttress plate, a second bone tunnel, and through the rotator cuff.

12. The method as defined in claim 11 wherein securing the suture relative to the buttress plate further includes tying the suture atop the buttress plate.

13. The method as defined in claim 8 further comprising forming a bone trough adjacent the entrance openings of the bone tunnels and positioning the rotator cuff within the bone trough.

14. The method as defined in claim 8 wherein providing the buttress plate further includes providing a buttress plate having an inner concave surface and an outer convex surface with the inner concave surface mating with an outer portion of the rotator cuff.

\* \* \* \* \*

UNITED STATES PATENT AND TRADEMARK OFFICE
CERTIFICATE OF CORRECTION

PATENT NO.    : 6,514,274 B1
DATED         : February 4, 2003
INVENTOR(S)   : James Boucher and Kevin J. Kessler It is certified that error appears in the above-identified patent and that said Letters Patent is hereby corrected as shown below:

Column 1,
Line 17, "overtime" should be -- over time --.

Column 3,
Line 46, after "will" insert -- the --.

Column 7,
Line 4, "puff" should be -- cuff --.

Signed and Sealed this

Seventeenth Day of June, 2003

JAMES E. ROGAN
*Director of the United States Patent and Trademark Office*